United States Patent
Jang

(10) Patent No.: US 10,449,106 B2
(45) Date of Patent: Oct. 22, 2019

(54) METHOD AND APPARATUS FOR WALKING ASSISTANCE

(71) Applicant: Samsung Electronics Co., Ltd., Suwon-si, Gyeonggi-do (KR)

(72) Inventor: Jun-Won Jang, Seoul (KR)

(73) Assignee: Samsung Electronics Co., Ltd., Gyeonggi-do (KR)

( * ) Notice: Subject to any disclaimer, the term of this patent is extended or adjusted under 35 U.S.C. 154(b) by 168 days.

(21) Appl. No.: 15/631,125

(22) Filed: Jun. 23, 2017

(65) Prior Publication Data

US 2018/0235831 A1    Aug. 23, 2018

(30) Foreign Application Priority Data

Feb. 21, 2017    (KR) .................. 10-2017-0022705

(51) Int. Cl.
| | | |
|---|---|---|
| *G05B 15/00* | (2006.01) | |
| *G05B 19/00* | (2006.01) | |
| *A61H 3/00* | (2006.01) | |
| *A61B 5/11* | (2006.01) | |
| *B25J 9/00* | (2006.01) | |
| *B62D 57/032* | (2006.01) | |
| *A61B 5/00* | (2006.01) | |
| *A61B 5/107* | (2006.01) | |

(Continued)

(52) U.S. Cl.
CPC ............ *A61H 3/00* (2013.01); *A61B 5/1071* (2013.01); *A61B 5/112* (2013.01); *A61B 5/6812* (2013.01); *A61B 5/6828* (2013.01); *A61B 5/7264* (2013.01); *A61B 5/7267* (2013.01); *B25J 9/0006* (2013.01); *B62D 57/032* (2013.01); *A61B 5/0488* (2013.01); *A61B 5/1122* (2013.01); *A61B 5/4528* (2013.01); *A61B 2562/0219* (2013.01); *A61H 2201/5064* (2013.01); *A61H 2201/5071* (2013.01); *B25J 9/1694* (2013.01); *B25J 13/088* (2013.01); *Y10S 901/09* (2013.01); *Y10S 901/46* (2013.01)

(58) Field of Classification Search
CPC ............ A61B 5/112; A61H 2201/5064; A61H 2201/5071; A61H 3/00; B25J 13/088; B25J 9/0006; B25J 9/1694; Y10S 901/09; Y10S 901/46
See application file for complete search history.

(56) References Cited

U.S. PATENT DOCUMENTS

| | | | |
|---|---|---|---|
| 2009/0265018 A1 | 10/2009 | Goldfarb et al. | |
| 2010/0204627 A1* | 8/2010 | Kazerooni | A61F 5/00 602/16 |

(Continued)

FOREIGN PATENT DOCUMENTS

| | | |
|---|---|---|
| JP | 2007-136041 A | 6/2007 |
| JP | 2013-070785 A | 4/2013 |

(Continued)

*Primary Examiner* — Harry Y Oh
(74) *Attorney, Agent, or Firm* — Harness, Dickey & Pierce, P.L.C.

(57) ABSTRACT

Walking assistance apparatuses and methods of controlling the walking assistance apparatus are provided. The walking assistance apparatus may recognize a type of a gait task of a user, and may assist a gait of the user to be suitable for the recognized gait task. The walking assistance apparatus may recognize the gait task as various categories using a pre-trained recognizer.

14 Claims, 11 Drawing Sheets

(51) Int. Cl.
  *B25J 9/16* (2006.01)
  *B25J 13/08* (2006.01)
  *A61B 5/0488* (2006.01)

(56) References Cited

U.S. PATENT DOCUMENTS

| | | | |
|---|---|---|---|
| 2011/0066088 A1* | 3/2011 | Little | B25J 9/0006 |
| | | | 601/35 |
| 2012/0215140 A1 | 8/2012 | Hirata et al. | |
| 2012/0226203 A1* | 9/2012 | Nakashima | A61H 3/00 |
| | | | 601/34 |
| 2012/0310412 A1* | 12/2012 | Seo | B25J 9/0006 |
| | | | 700/254 |
| 2014/0114437 A1 | 4/2014 | Herr et al. | |
| 2014/0221894 A1* | 8/2014 | Nagasaka | A61H 3/00 |
| | | | 602/23 |
| 2014/0277739 A1* | 9/2014 | Kornbluh | B25J 9/0006 |
| | | | 700/260 |
| 2015/0134080 A1* | 5/2015 | Roh | B25J 9/0006 |
| | | | 623/32 |
| 2015/0196403 A1* | 7/2015 | Kim | A61F 2/70 |
| | | | 623/24 |
| 2016/0358099 A1 | 12/2016 | Sturlaugson et al. | |

FOREIGN PATENT DOCUMENTS

| | | |
|---|---|---|
| KR | 10-1490885 B1 | 2/2015 |
| KR | 10-2015-0053854 A | 5/2015 |
| KR | 10-2016-0014284 A | 2/2016 |
| KR | 10-2016-0096460 A | 8/2016 |

\* cited by examiner

METHOD AND APPARATUS FOR WALKING ASSISTANCE

CROSS-REFERENCE TO RELATED APPLICATION

This application claims priority under 35 U.S.C. § 119 to Korean Patent Application No. 10-2017-0022705, filed on Feb. 21, 2017, in the Korean Intellectual Property Office, the entire contents of which are incorporated herein by reference.

BACKGROUND

1. Field

At least one example embodiment relates to a technology for recognizing a gait task and controlling a walking assistance apparatus.

2. Description of the Related Art

With the increasing onset of the aging society, the elderly and/or patients having joint issues are increasing. Accordingly, interest on walking assistance apparatuses that enable the elderly and/or patients having such joint issues to walk with less effort is also increasing. Further, walking assistance apparatuses for assisting muscular strength of users for, for example, military purposes are being developed.

For example, a walking assistance apparatus includes a body frame provided to a torso of a user, a pelvis frame configured to couple with a lower side of the body frame and to surround a pelvis of the user, and a thigh frame, a calf frame, and a foot frame provided to a thigh, and a foot area of the user. For example, the pelvis frame and the thigh frame are rotatably connected by a hip joint portion, and the thigh frame and the calf frame are rotatably connected by a knee joint portion, and the calf frame and the foot frame are rotatably connected by an ankle joint.

SUMMARY

Some example embodiments relate to a method of controlling a walking assistance apparatus.

In some example embodiment, the walking assistance apparatus controlling method may include determining whether a foot of a user wearing the walking assistance apparatus, which is configured to measure a joint motion of the user, is in contact with ground, determining a first gait task of the user based on first joint motion information, the first joint motion information associated with a contact point in time at which the foot is in contact with the ground, determining a second gait task of the user based on second joint motion information, the second joint motion information associated with the first gait task and the contact point in time, and controlling the walking assistance apparatus based on at least one of the first gait task or the second gait task.

The first joint motion information may include at least one of a left hip joint angle associated with the contact point in time, a right hip joint angle associated with the contact point in time, or a difference between the left hip joint angle and the right hip joint angle.

The determining whether the foot of the user is in contact with the ground may include determining whether the foot of the user is in contact with the ground based on third joint motion information, the third joint motion information measured in a remaining time period, the remaining time period being a time period excluding a certain time period after a previous contact point in time from a time period between the previous contact point in time and a current contact point in time.

The third joint motion information may include a vertical acceleration of a pelvis.

The determining whether the foot of the user is in contact with the ground may include determining a point in time at which an average acceleration in the remaining time period is greater than or equal to a threshold as the current contact point in time.

The determining a first gait task may comprise determining the first gait task as an ascending motion, a descending motion, or a parallel motion, and the determining a second gait task may comprise determining the second gait task as a step-ascending motion or a slope-ascending motion in response to the first gait task determined as the ascending motion, determining the second gait task as a step-descending motion or a slope-descending motion in response to the first gait task determined as the descending motion, and determining the second gait task as the slope-ascending motion, the slope-descending motion, or the parallel motion in response to the first gait task determined as the parallel motion.

The second joint motion information may include at least one of a difference between a hip joint angle and a knee angle on a side on which the foot is in contact with the ground, a larger value between left and right knee angles, or a difference between left and right ankle angles in response to the first gait task determined as the ascending motion. The second joint motion information may include an average speed of an ankle on the side on which the foot is in contact with the ground during a period of time before the contact point in time in response to the first gait task is determined as the descending motion. The second joint motion information may include at least one of a ratio between a hip joint angle and a knee angle on the side on which the foot is in contact with the ground, a difference between the left and right knee angles, a minimum value or a maximum value of left and right hip joint angles, or a ratio between a knee angle at a point in time at which the left and right knee angles become equal and a maximum value of the knee angle in response to the first gait task is determined as the parallel motion.

The determining a first gait task may include determining the first gait task as an ascending motion, a descending motion, or a parallel motion, and the determining a second gait task may comprise determining the second gait task as a slope-ascending motion, a slope-descending motion, or the parallel motion in response to the first gait task determined as the parallel motion.

The second joint motion information may include at least one of a ratio between a hip joint angle and a knee angle on a side on which the foot is in contact with the ground, a difference between left and right knee angles, a minimum value or a maximum value of left and right hip joint angles, or a ratio between a knee angle at a point in time at which the left and right knee angles become equal and a maximum value of the knee angle.

The determining a first gait task may comprise determining the first gait task as an ascending motion, a descending motion, or a parallel motion, and the determining a second gait task may comprise determining the second gait task as a step-ascending motion or a slope-ascending motion in response to the first gait task determined as the ascending motion, and determining the second gait task as a step-descending motion or a slope-descending motion in response to the first gait task determined as the descending motion.

The determining a first gait task may comprise determining the first gait task as an up-and-down motion or a parallel motion, and the determining a second gait task may comprise determining the second gait task as an ascending motion or a descending motion in response to the first gait task determined as the up-and-down motion.

The walking assistance apparatus controlling method may further include determining a third gait task of the user based on third joint motion information, the third joint motion information associated with the second gait task and the contact point in time. The controlling may include controlling the walking assistance apparatus based on the first gait task, second gait task, and third gait task, the determining a first gait task may include determining the first gait task as an up-and-down motion or a parallel motion, the determining a second gait task may include determining the second gait task as an ascending motion or a descending motion in response to the first gait task determined as the up-and-down motion, and the determining a third gait task may include determining the third gait task as a step-ascending motion or a slope-ascending motion in response to the second gait task determined as the ascending motion, and determining the third gait task as a step-descending motion or a slope-descending motion in response to the second gait task determined as the descending motion.

The determining whether the foot of the user is in contact with the ground may include determining whether the foot is in contact with the ground based on foot sensor information measured from a foot sensor included in the walking assistance apparatus.

A non-transitory computer-readable recording medium may store a program, which when executed by a computer, configures the computer to perform the walking assistance apparatus controlling method set forth above.

Some example embodiments relate to a walking assistance apparatus.

In some example embodiments, the walking assistance apparatus may include a memory configured to store computer-readable instructions, and at least one processor configured to execute the computer-readable instructions such that the at least one processor is configured to determine whether a foot of a user wearing the walking assistance apparatus, which is configured to measure a joint motion of the user, is in contact with ground, determine a first gait task of the user based on first joint motion information, the first joint motion information associated with a contact point in time at which the foot is in contact with the ground, determine a second gait task of the user based on second joint motion information, the second joint motion information associated with the first gait task and the contact point in time, and control the walking assistance apparatus based on at least one of the first gait task or the second gait task.

Additional aspects of example embodiments will be set forth in part in the description which follows and, in part, will be apparent from the description, or may be learned by practice of the disclosure.

BRIEF DESCRIPTION OF THE DRAWINGS

These and/or other aspects of the inventive concepts will become apparent and more readily appreciated from the following description of some example embodiments, taken in conjunction with the accompanying drawings of which.

DETAILED DESCRIPTION

Figure 1:
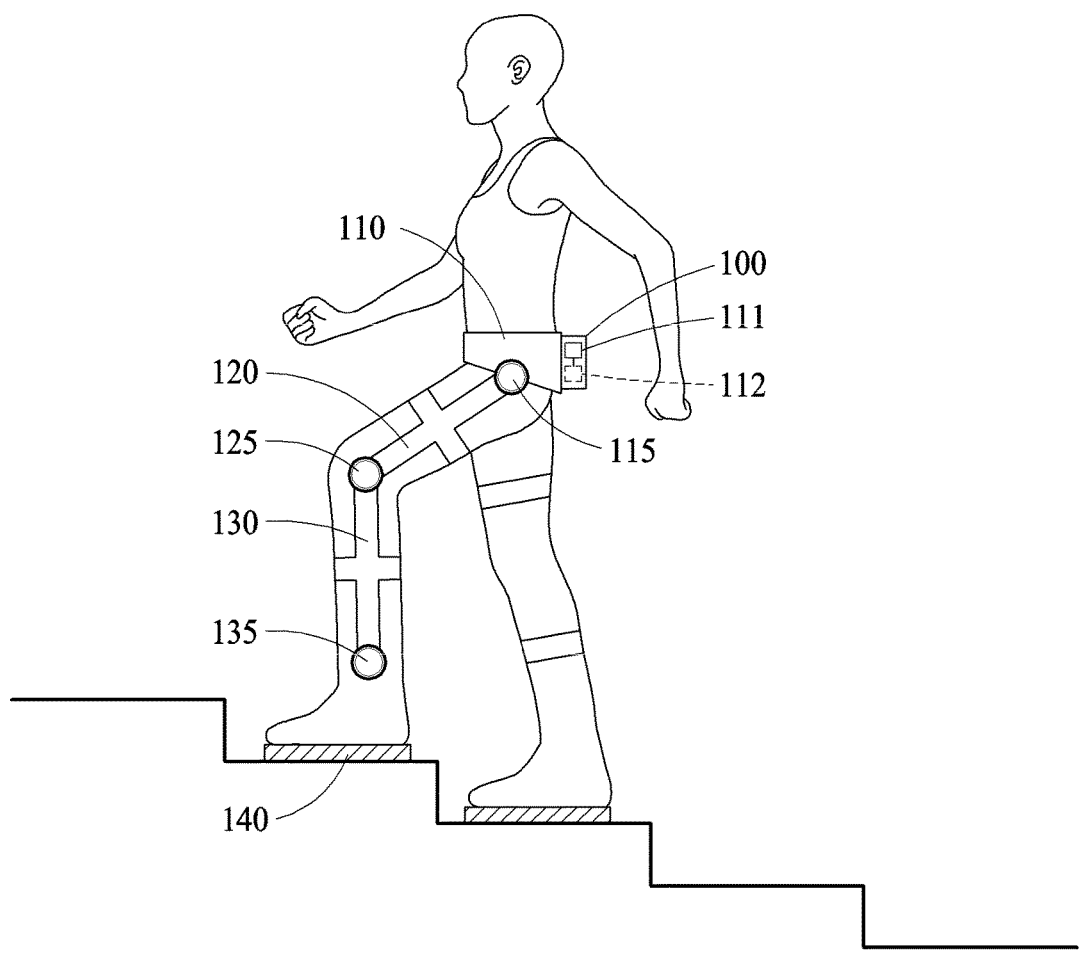
FIG. 1 illustrates a configuration of a walking assistance apparatus according to at least one example embodiment.

Hereinafter, some example embodiments will be described in detail with reference to the accompanying drawings. Regarding the reference numerals assigned to the elements in the drawings, it should be noted that the same elements will be designated by the same reference numerals, wherever possible, even though they are shown in different drawings. Also, in the description of example embodiments, detailed description of well-known related structures or functions will be omitted when it is deemed that such description will cause ambiguous interpretation of the present disclosure.

It should be understood, however, that there is no intent to limit this disclosure to the particular example embodiments disclosed. On the contrary, example embodiments are to cover all modifications, equivalents, and alternatives of the disclosed example embodiments. Like numbers refer to like elements throughout the description of the figures.

In addition, terms such as first, second, A, B, (a), (b), and the like may be used herein to describe components. Each of these terminologies is not used to define an essence, order, or sequence of a corresponding component, but used merely to distinguish the corresponding component from other component(s). It should be noted that if it is described in the specification that one component is "connected", "coupled", or "joined" to another component, a third component may be "connected", "coupled", and "joined" between the first and second components, although the first component may be directly connected, coupled or joined to the second component.

The terminology used herein is for the purpose of describing particular example embodiments only and is not intended to be limiting. As used herein, the singular forms "a," "an," and "the," are intended to include the plural forms as well, unless the context clearly indicates otherwise. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

Unless otherwise defined herein, all terms used herein including technical or scientific terms have the same meanings as those generally understood by one of ordinary skill in the art. Terms defined in generally used dictionaries should be construed to have meanings matching with contextual meanings in the related art, and are not to be construed as an ideal or excessively formal meaning unless otherwise defined herein.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

As used herein, the term "and/or" includes any and all combinations of one or more of the associated listed items. Expressions such as "at least one of" and "one of" when preceding a list of elements, modify the entire list of elements and do not modify the individual elements of the list. Thus, for example, both "at least one of A, B, or C" and "A, B, and/or C" means either A, B, C or any combination thereof.

Various example embodiments will now be described more fully with reference to the accompanying drawings in which some example embodiments are shown. In the drawings, the thicknesses of layers and regions are exaggerated for clarity.

FIG. 1 illustrates a configuration of a walking assistance apparatus according to at least one example embodiment.

Referring to FIG. 1, the walking assistance apparatus may recognize a gait task of a user wearing the walking assistance apparatus and may assist a walking of the user to be suitable for the recognized gait task. For example, the walking assistance apparatus may recognize various types of gait tasks using a pre-trained recognizer. Here, the walking assistance apparatus may precisely recognize the gait task based on a variety of sensor information. In one example embodiment, the walking assistance apparatus may be used to assist the rehabilitation of a patient suffering from a degraded lower body function or to assist or strengthen a lower body function of a laborer. The walking assistance apparatus may be used to improve the physical capability of a soldier.

In one example embodiment, the walking assistance apparatus may include exoskeletons 110, 120, and 130 each configured to support a lower body, sensors 115, 125, and 135 each configured to measure joint motion information between the respective exoskeletons, and a controller 100. The controller 100 may control the exoskeletons 110, 120, and 130 and the sensors 115, 125, and 135.

Here, the exoskeletons 110, 120, and 130 configured to support the lower body may include a hip exoskeleton, a knee exoskeleton, an ankle exoskeleton, a hip-knee exoskeleton, a hip-ankle exoskeleton, a knee-ankle exoskeleton, and/or a hip-knee-ankle exoskeleton.

A sensor configured to measure joint motion information may be present in each joint portion of the walking assistance apparatus. For example, the walking assistance apparatus may include the sensor 115 configured to measure joint motion information of a hip joint, the sensor 125 configured to measure joint motion information of a knee, and/or the sensor 135 configured to measure joint motion information of an ankle. The aforementioned exoskeletons and sensors may be configured in the walking assistance apparatus through various combinations.

The controller 100 may be connected to or separate from the exoskeletons 110, 120, and/or 130 and the sensors 115, 125, and/or 135. The controller 100 may be attached to another part of a body, for example, a wrist. For example, the controller 100 may be provided in a form of a terminal (e.g., a smartphone).

The controller 100 may include a processor 111. The processor 111 may determine whether a foot of the user wearing the walking assistance apparatus (e.g., a lower-limb exoskeleton) is in contact with the ground. The walking assistance apparatus may measure information about a joint motion of the user. The processor 111 may estimate a contact point in time at which the foot is in contact with the ground, and may determine a gait task based on joint motion information associated with the estimated contact point in time. A type of a gait task at a single point in time may be recognized through a plurality of phases. At each phase, a different piece of joint motion information and a different recognizer may be used. Determining the gait task may be gradually embodied by passing through the respective phases.

The controller 100 may further include a memory 112. The memory 112 may store instructions, which when executed by the processor 111, configures the processor 111 to perform desired operations. The memory 112 may store control information for controlling the walking assistance apparatus based on the joint motion information measured by the walking assistance apparatus and the type of the gait task determined by the processor 111.

Because the gait task is determined based on joint motion information associated with the contact point in time at which the foot is in contact with the ground, whether the foot is in contact with the ground is to be determined first. The walking assistance apparatus may determine whether the foot is in contact with the ground based on joint motion information of the user. As another example, the walking assistance apparatus may further include a foot sensor 140 configured to measure whether the foot is in contact with the ground, and may determine whether the foot is in contact with the ground based on information sensed at the foot sensor 140.

The walking assistance apparatus may recognize various types of gait tasks based on a variety of sensor information using a plurality of recognizers. Here, the sensor information may include information acquired during a desired (or alternatively, predetermined) time period before and after a point in time at which the foot is in contact with the ground. The sensor information may include joint motion information measured by the walking assistance apparatus. The joint motion information may include hip joint motion information, knee motion information, and/or ankle motion information. Here, the joint motion information may include a location of each joint, a difference between locations of joints, acceleration, angular velocity, and/or a value calculated based thereon.

The walking assistance apparatus may assist a walking of the user through a motion corresponding to a type of a gait task. For example, the type of the gait task may be classified into a parallel motion, an ascending motion, a descending motion, an up-and-down motion, a slope-ascending motion, a slope-descending motion, a step-ascending motion, a step-descending motion. However, examples of types of gait tasks are not limited thereto.

In one example embodiment, the walking assistance apparatus may perform a plurality of motion modes corresponding to a plurality of gait tasks, respectively. Every time the user makes a gait, the walking assistance apparatus may recognize a type of a corresponding gait task and the walking assistance apparatus may be controlled in a motion mode corresponding to the recognized type of the gait task.

As described above, the walking assistance apparatus may further precisely control walking assistance by determining the type of the gait task. Further, the walking assistance apparatus may recognize the type of the gait task based on joint motion information of the hip joint as well as joint motion information of one or more other joints. Thus, the walking assistance apparatus may recognize the type of the gait task even when the walking assistance apparatus does not include the sensor 115 for measuring hip joint motion information. Further, although the foot sensor 140 is not included in the walking assistance apparatus, the walking assistance apparatus may determine a contact point in time at which the foot is in contact with the ground based on joint motion information measured using one or more other sensors, and may use joint motion information having a relatively high accuracy, which is measured before and/or after the contact point in time, as input information.

Figure 2:
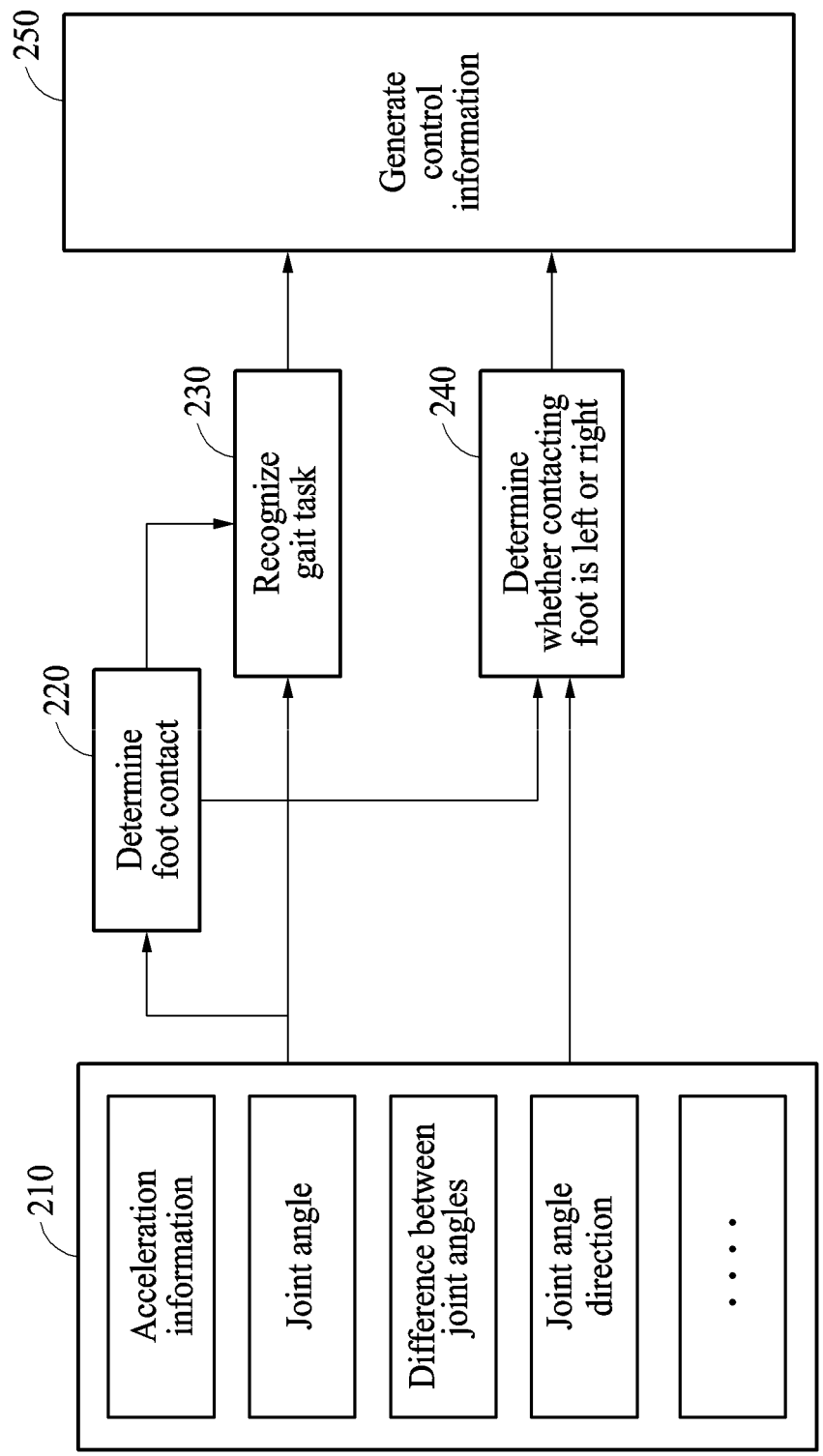
FIG. 2 illustrates an operation of recognizing a gait task and generating control information for a walking assistance according to at least one example embodiment.

FIG. 2 illustrates an operation of recognizing a gait task and generating control information for a walking assistance according to at least one example embodiment.

Referring to FIG. 2, in operation 210, the walking assistance apparatus may receive a variety of joint motion information from the sensors 115, 125, and 135. For example, the walking assistance apparatus may receive the joint motion information, which includes acceleration information, a joint angle, a difference between joint angles, and a joint angle direction.

In operation 220, the walking assistance apparatus may determine whether a foot of a user wearing the walking assistance apparatus is in contact with the ground based on the joint motion information. The walking assistance apparatus may determine whether the foot is in contact with the ground based on information received from the foot sensor 140.

In operation 230, the walking assistance apparatus may recognize a gait task based on joint motion information measured during a desired (or alternatively, predetermined) time period around (e.g., before and/or after) a contact point in time at which the foot is in contact with the ground. The gait task recognition may be performed through a plurality of phases. A different piece of joint motion information may be used for each phase and different recognizers each for determining a different type of a gait task may be used. A type of a gait task may be embodied from an upper concept of a gait task to a lower concept of a gait task while passing through each phase.

In operation 240, the walking assistance apparatus may determine whether the foot in contact with the ground is a left foot or a right foot. Joint motion information used to determine whether the foot is in contact with the ground may include left and right information indicating the foot in contact with the ground. The walking assistance apparatus may determine whether the contacting foot is the left foot or the right foot based on the left and right information. Here, the left and right information of the contacting foot may refer to information indicating whether the foot in contact with the ground is the left foot or the right foot.

In operation 250, the walking assistance apparatus may generate control information for controlling the walking assistance apparatus based on the recognized gait task and the left and right information of the contacting foot. For example, the walking assistance apparatus may determine that the left foot is in contact with the ground, and generate control information for controlling the walking assistance apparatus to perform a step-ascending motion of the left foot.

Figure 3:
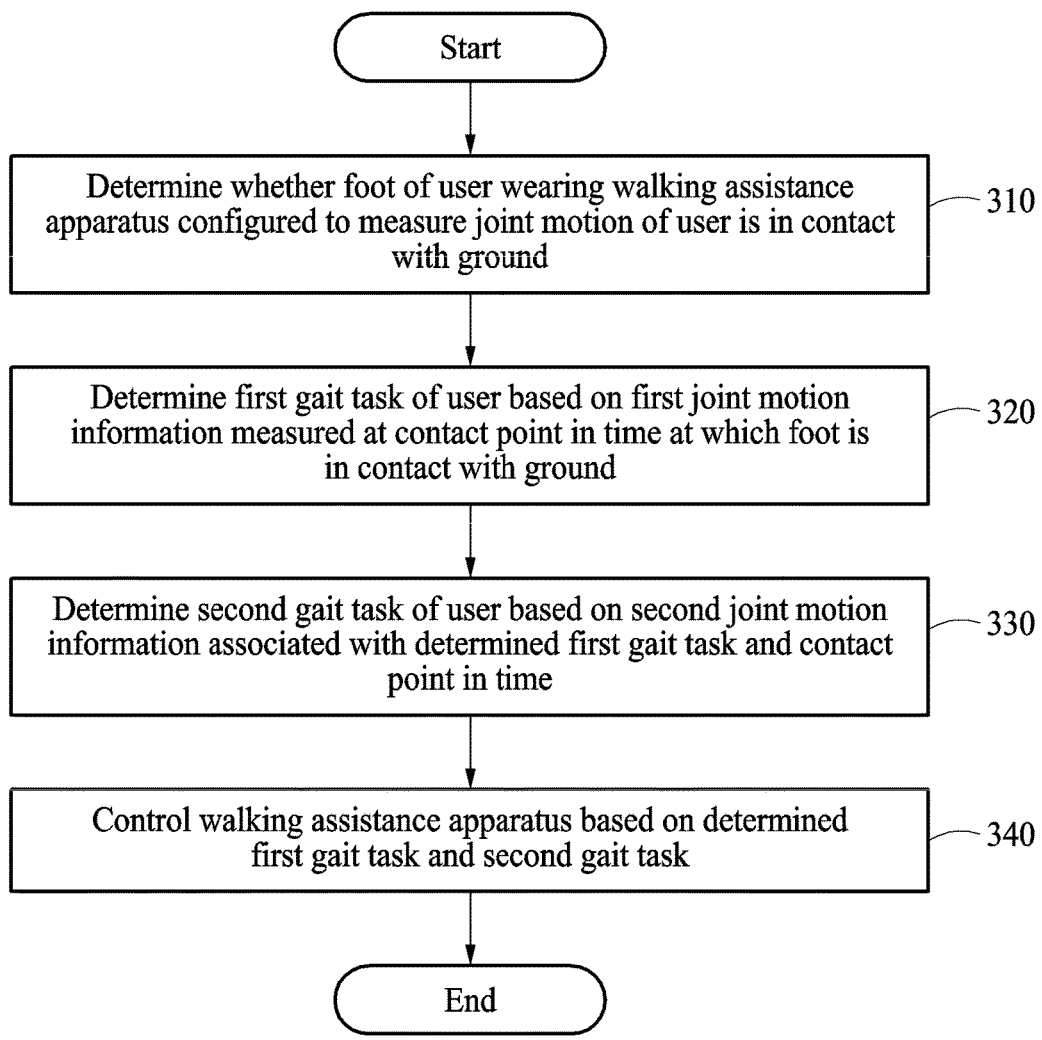
FIG. 3 is a flowchart illustrating a method of controlling a walking assistance apparatus according to at least one example embodiment.

FIG. 3 illustrates a method of controlling a walking assistance apparatus according to at least one example embodiment.

Referring to FIG. 3, in operation 310, the walking assistance apparatus may determine whether a foot of a user wearing the walking assistance apparatus, which is configured to measure a joint motion of the user, is in contact with the ground. The walking assistance apparatus may determine a point in time at which the foot is in contact with the ground based on the joint motion information.

In operation 320, the walking assistance apparatus may determine a first gait task of the user based on first joint motion information associated with the contact point in time at which the foot is in contact with the ground. The first joint motion information may indicate information associated with a state or a motion of a lower body joint. Here, the lower body joint may include a hip joint, a knee joint, and/or an ankle joint.

For example, the first joint motion information may include a left hip joint angle associated with the contact point in time, a right hip joint angle associated with the contact point in time, and/or a difference between the left hip joint angle and the right hip joint angle. As another example, the first joint motion information may include a knee angle at a point in time at which angles of left and right knee joints become equal, a ratio between a hip joint angle and a knee joint angle, a ratio between a knee angle at a point in time at which angles of left and right knee joint become equal and a maximum value of a knee angle, a vertical acceleration of a pelvis, a difference between a hip joint angle and a knee angle on a side on which the foot is in contact with the ground, a larger value between left and right knee angles or a difference between left and right ankle angles, an average speed of an ankle on the side on which the foot is in contact with the ground during a desired (or alternatively, predetermined) period of time before the contact point in time, a ratio between the knee angle and the hip joint angle on the side on which the foot is in contact with the ground, a difference between the left and right knee angles, a minimum value or a maximum value of left and right hip joint angle, and/or a ratio between a knee angle at a point in time at which the left and right knee angles become equal and a maximum value of the knee angle. However, examples of the first joint motion information are not limited thereto.

In operation 330, the walking assistance apparatus may determine a second gait task of the user based on second joint motion information associated with the determined first gait task and the contact point in time. Here, the first joint motion information and the second joint motion information may differ from each other. The first gait task may be included in an upper concept category compared to the second gait task. The second joint motion information may refer to information associated with a state or a motion of a lower body joint. The second joint motion information may include information that is not included in the first joint motion information, which is determined prior to determining the second joint motion information.

For example, the second joint motion information may include a left hip joint angle associated with the contact point in time, a right hip joint angle associated with the contact point in time, or a difference between the left hip joint angle and the right hip joint angle. As another example, the second joint motion information may include a knee angle at a point in time at which angles of left and right knee joint become equal, a ratio between a hip joint angle and a knee joint angle, a ratio between a knee angle at a point in time at which angles of left and right knee joint become equal and a maximum value of a knee angle, a vertical acceleration of a pelvis, a difference between a hip joint angle and a knee angle on a side on which the foot is in contact with the ground, a larger value between left and right knee angles or a difference between left and right ankle angles, an average speed of an ankle on a side on which the foot is in contact with the ground during a desired (or alternatively, predetermined) period of time before the contact point in time, a ratio between the knee angle and the hip joint angle on the side on which the foot is in contact with the ground, a difference between the left and right knee angles, a minimum value or a maximum value of left and right hip joint angle, and/or a ratio between a knee angle at a point in time at which the left and right knee angles become equal and a maximum value of the knee angle. However, examples of the second joint motion information are not limited thereto.

A process of determining the type of the gait task in operations 320 and 330 may be performed using a plurality of recognizers. The recognizers may estimate a gait task based on joint motion information associated with the contact point in time. A type of a final gait task may be determined based on combination of execution results of the recognizers.

The recognizers used to estimate or recognize a type of a gait task may be trained, for example, in advance, by machine learning. Learning parameters for a desired (or alternatively, predetermined) learning model may be extracted by applying a gait feature of each of a plurality of pieces of gait data to the learning model that is set or predetermined for the machine learning. Here, the learning model may include at least one of a neural network (NN) model, a support vector machine (SVM) model, and a Gaussian mixture model. In some example embodiments, the learning model may include a pattern classification based learning model capable of estimating a gait task using a feature vector, the neural network model, a support vector recursive model, or a Gaussian process recursive model.

When the learning model is the neural network model, the learning parameters may include a connection pattern between neurons, weights, and activation functions. When the learning model is the support vector recursive model, the learning parameters may include kernel functions and penalty parameters. When the learning model is the Gaussian process recursive model, the learning parameters may include kernel functions and hyper-parameters.

Different input information may be input to a recognizer for each recognition phase. The learning parameters for the learning model may be extracted from input information that is desired (or alternatively, preset) for each recognizer. For example, machine learning may be performed on a recognizer for determining the first gait task based on learning parameters extracted from first joint motion information. Machine learning may be performed on a recognizer for determining the second gait task based on learning parameters extracted from second joint motion information.

Joint motion information may indicate data sensed from, for example, the momentum of the user, and/or a change in biosignals of the user according to a gait motion using a sensor attached to the walking assistance apparatus. The sensing data may include at least one of acceleration data sensed by an inertial measurement unit (IMU) sensor, angular velocity data, joint angle data sensed by a potentiometer, joint angular velocity data, or electromyography (EMG) data sensed by an EMG sensor.

Acceleration data or angular velocity data may indicate acceleration data or angular velocity data about at least a portion of axes X, Y, and Z. Also, joint angle data or joint angular velocity data may indicate joint angle data or joint angular velocity data about at least a portion of a right axis and a left axis. Sensing data may be extracted from a plurality of IMU sensors, a plurality of potentiometers, and/or a plurality of EMG sensors. However, example embodiments are not limited thereto. Thus, without being limited to the IMU sensor, the potentiometer, or the EMG sensor, any type of sensors capable of sensing, for example, the momentum of the user, and/or a change in biosignals according to a gait motion may be applied.

The walking assistance apparatus may construct a plurality of databases by classifying a plurality of gait patterns based on a plurality of gait tasks, and by storing the classified plurality of gait patterns into the plurality of databases corresponding to the plurality of gait tasks as a plurality of items of gait data, respectively.

For example, a type of a gait task may include a parallel motion, a slope-ascending motion, a slope-descending motion, a step-ascending motion, and a step-descending motion. As another example, the type of the gait task may be classified into three categories (e.g., the parallel motion, the slope-ascending motion, and the slope-descending motion). As still another example, the type of the gait task may be classified into seven types (e.g., the parallel motion, a 15-degree-slope-ascending motion, a 30-degree-slope-ascending motion, a 15-degree-slope-descending motion, a 30-degree-slope-descending motion, the step-ascending motion, and the step-descending motion). However, example embodiments are not limited thereto, and the gait task may be classified into further categories.

In operation 340, the walking assistance apparatus may control the walking assistance apparatus based on the determined first gait task or second gait task. The walking assistance apparatus may determine the type of the gait task of the user as the first gait task and may control the walking assistance apparatus in a gait mode corresponding to the determined first gait task. Further, the walking assistance apparatus may determine the type of the gait task of the user as the second gait task that is further classified from the first gait task and may control the walking assistance apparatus in a gait mode corresponding to the determined second gait task.

Figure 4:
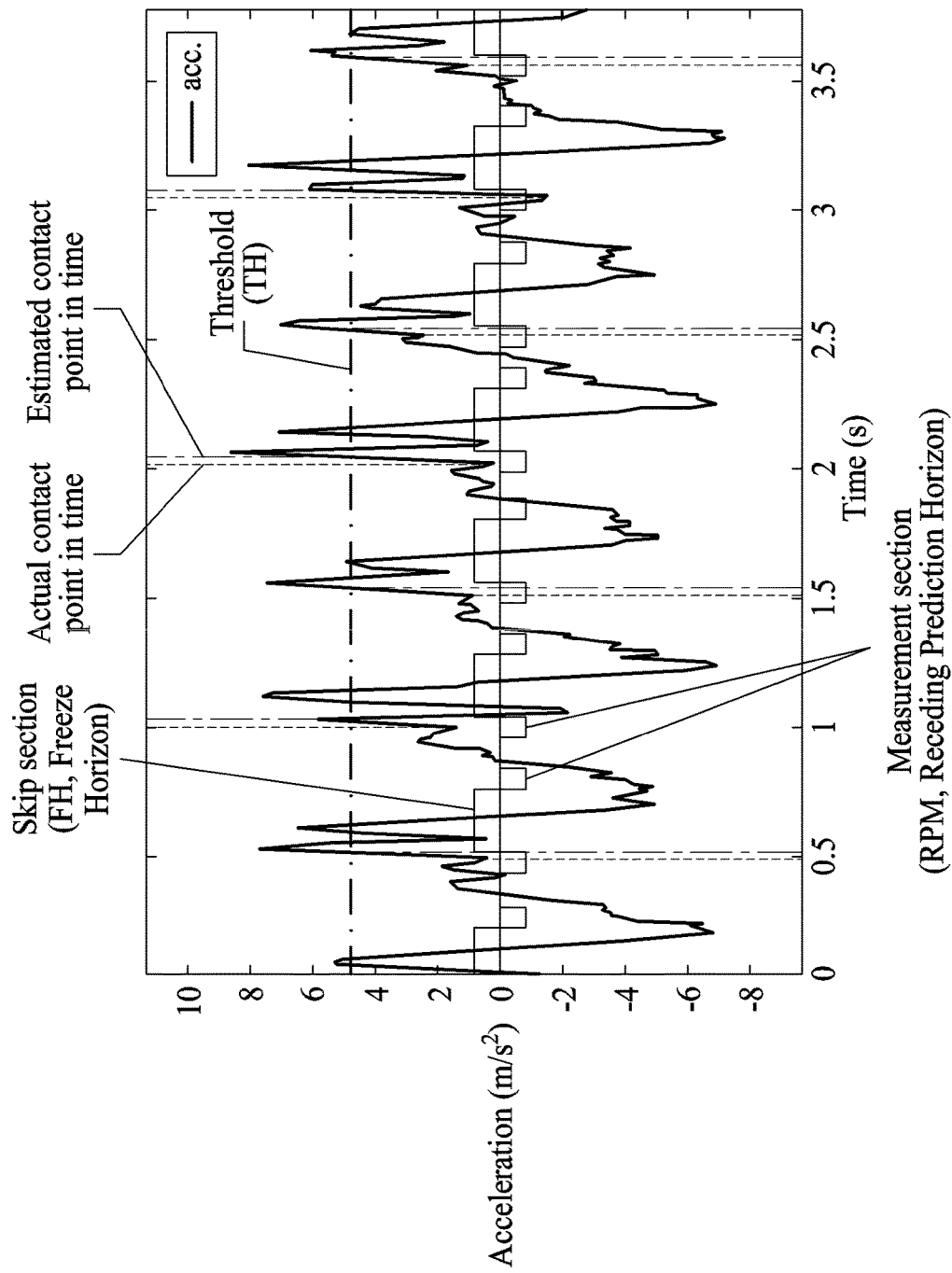
FIG. 4 illustrates an example of a graph to determine whether a foot is in contact with ground according to at least one example embodiment.

FIG. 4 illustrates an example of a graph to determine whether a foot is in contact with the ground according to at least one example embodiment.

The walking assistance apparatus may determine whether the foot of the user is in contact with the ground without using the foot sensor 140. In some example embodiments, the walking assistance apparatus may determine whether the foot is in contact with the ground based on pelvis motion information sensed using an acceleration sensor attached to a pelvis of the user.

The walking assistance apparatus may determine whether the foot of the user is in contact with the ground based on third joint motion information, which has been measured in a remaining time period, which is a time period excluding a desired (or alternatively, predetermined) time period after a previous contact point in time from a time period between the previous contact point in time and a current contact point in time.

Here, the desired (or alternatively, predetermined) time period may be referred to as a skip section (e.g., a freeze horizon (FH)), and the remaining time period may be referred to as a measurement section (e.g., a receding prediction horizon (RPM)). A desired (or alternatively, predetermined) period of time after the contact point in time of the foot may be set as the skip section (e.g., the FH), and determining whether the foot is in contact with the ground may not be performed in the skip section (e.g., the FH). A concept of the skip section (e.g., the FH) is taken into consideration that when the user walks, a certain amount of time is required until a subsequent foot contact point in time after a current foot contact is applied to. By introducing the skip section (e.g., the FH), it is possible to reduce a time section for sensing and measuring a foot contact. Further, because the measurement is performed in a time section in which the foot contact is highly likely to occur, the accuracy of the measurement may increase.

The third joint motion information may be different from the joint motion information used to determine the first gait task or the second gait task. For example, the third joint motion information may include a vertical acceleration of the pelvis.

The walking assistance apparatus may determine a point in time at which an average acceleration in the remaining time section is greater than or equal to a desired (or alternatively, preset) threshold TH as a current contact point in time. For example, the walking assistance apparatus may determine whether an average acceleration value corresponding to a measurement section (e.g., an RPM), associated with the vertical direction among acceleration values generated at the acceleration sensor is greater than or equal to the threshold TH. Referring to FIG. 4, a deviation between a contact point in time estimated using this method and an actual contact point in time may be insignificant.

As described above, although the walking assistance apparatus does not include the foot sensor 140, the walking assistance apparatus may appropriately control a gait motion of a user. Thus, example embodiments may be applicable to various types of walking assistance apparatuses.

Figure 5:
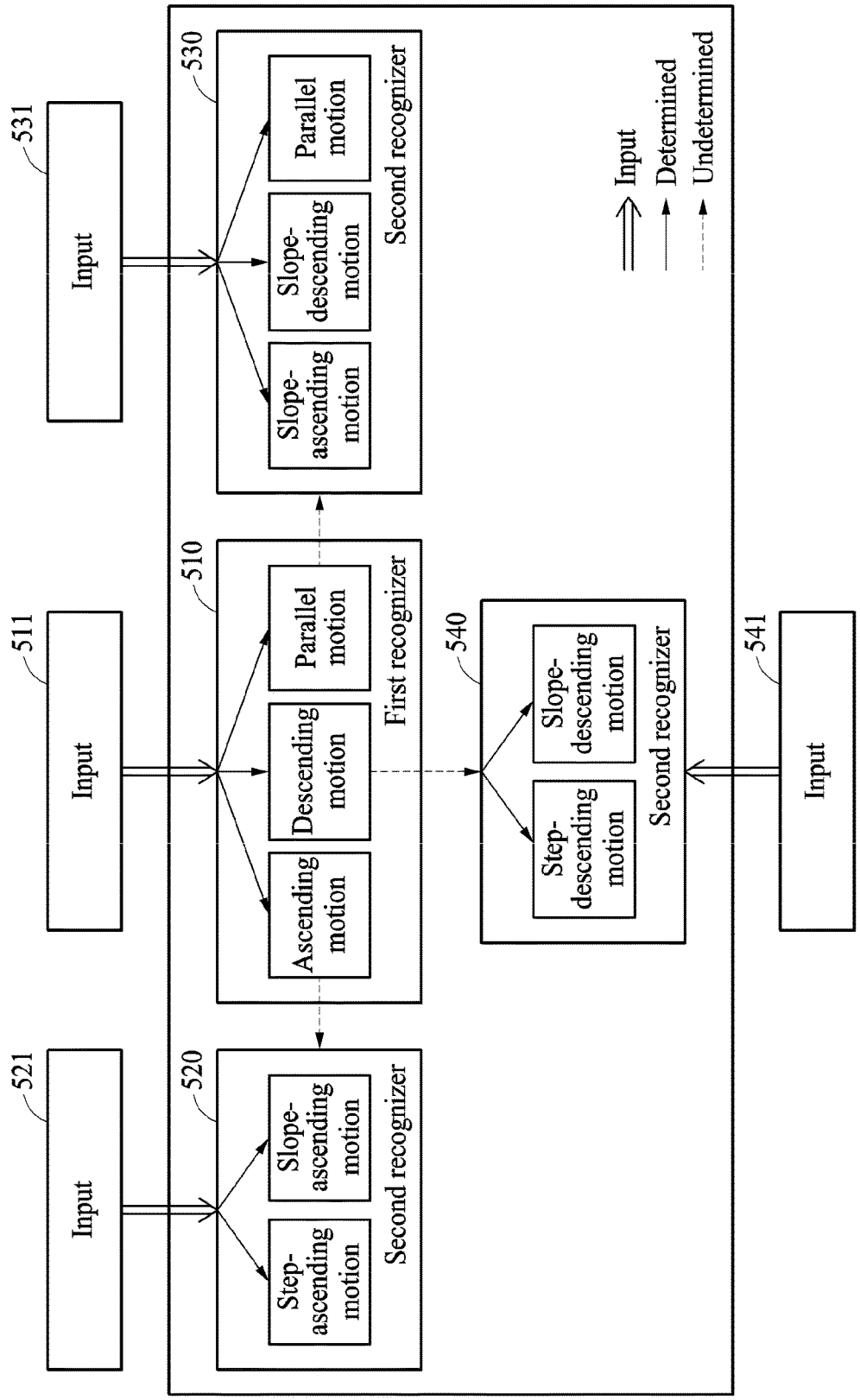
FIG. 5 illustrates an example of a method of controlling a walking assistance apparatus according to at least one example embodiment.

FIG. 5 illustrates an example of a method of controlling a walking assistance apparatus according to at least one example embodiment.

FIG. 5 illustrates an example embodiment of performing a second recognition phase with respect to a first recognition phase, which recognizes a gait motion of a user as one of an ascending motion, a descending motion, or a parallel motion. In this example embodiment, the walking assistance apparatus may determine a type of a gait task of a user as one of a step-ascending motion, a step-descending motion, a slope-ascending motion, a slope-descending motion, or the parallel motion by sequentially performing the first recognition phase and the second recognition phase. The walking assistance apparatus may perform category classification into the ascending motion, the descending motion, or the parallel motion, and may determine a detailed scheme with respect to each category.

When a foot of the user is determined to be in contact with the ground, the walking assistance apparatus may determine a first gait task as the ascending motion, the descending motion, or the parallel motion using a first recognizer 510. An input 511 may indicate first joint motion information.

The walking assistance apparatus may determine a motion, from among the ascending motion, the descending motion, and the parallel motion, which is similar to the gait task of the user, based on the first joint motion information using the first recognizer 510. For example, the first recognizer 510 may be trained by machine learning based on, for example, a left hip joint angle, a right hip joint angle, and/or a difference between the left and right hip joint angles.

When the first gait task is determined as the ascending motion, the walking assistance apparatus may determine a second gait task as the step-ascending motion or the slope-ascending motion using a first-second recognizer 520. Here, an input 521 may indicate first-second joint motion information. The first-second joint motion information may include a difference between a knee angle and a hip joint angle on a side on which the foot is in contact with the ground, a larger value between left and right knee angles, and/or a difference between left and right ankle angles.

When the first gait task is determined as the descending motion, the walking assistance apparatus may determine the second gait task as the step-descending motion or the slope-descending motion using a second-second recognizer 540. Here, an input 541 may indicate second-second joint motion information. The second-second joint motion information may include an average speed of an ankle on the side on which the foot is in contact with the ground during a desired (or alternatively, predetermined) period of time before the contact point in time. For example, the period of time may be 50 ms.

When the first gait task is determined as the parallel motion, the walking assistance apparatus may determine the second gait task as the slope-ascending motion, the slope-descending motion, or the parallel motion using a third-second recognizer 530. Here, an input 531 may indicate third-second joint motion information. The third-second joint motion information may include a ratio between a hip joint angle and a knee angle on the side on which the foot is in contact with the ground, a difference between the left and right knee angles, a minimum value or a maximum value of left and right hip joint angles, and/or a ratio between a knee angle at a point in time at which the left and right knee angles become equal and a maximum value of the knee angle.

Although it is described that the first recognizer 510 is used to classify the ascending motion, the descending motion, and the parallel motion, it is provided as an example only. For example, the first recognizer 510 may determine the first gait task as the step-ascending motion, the step-descending motion, or the parallel motion. In some example embodiments, the first recognizer 510 may determine the first gait task as the step-ascending motion, the step-descending motion, the slope-ascending motion, the slope-descending motion, or the parallel motion.

Figure 6A:
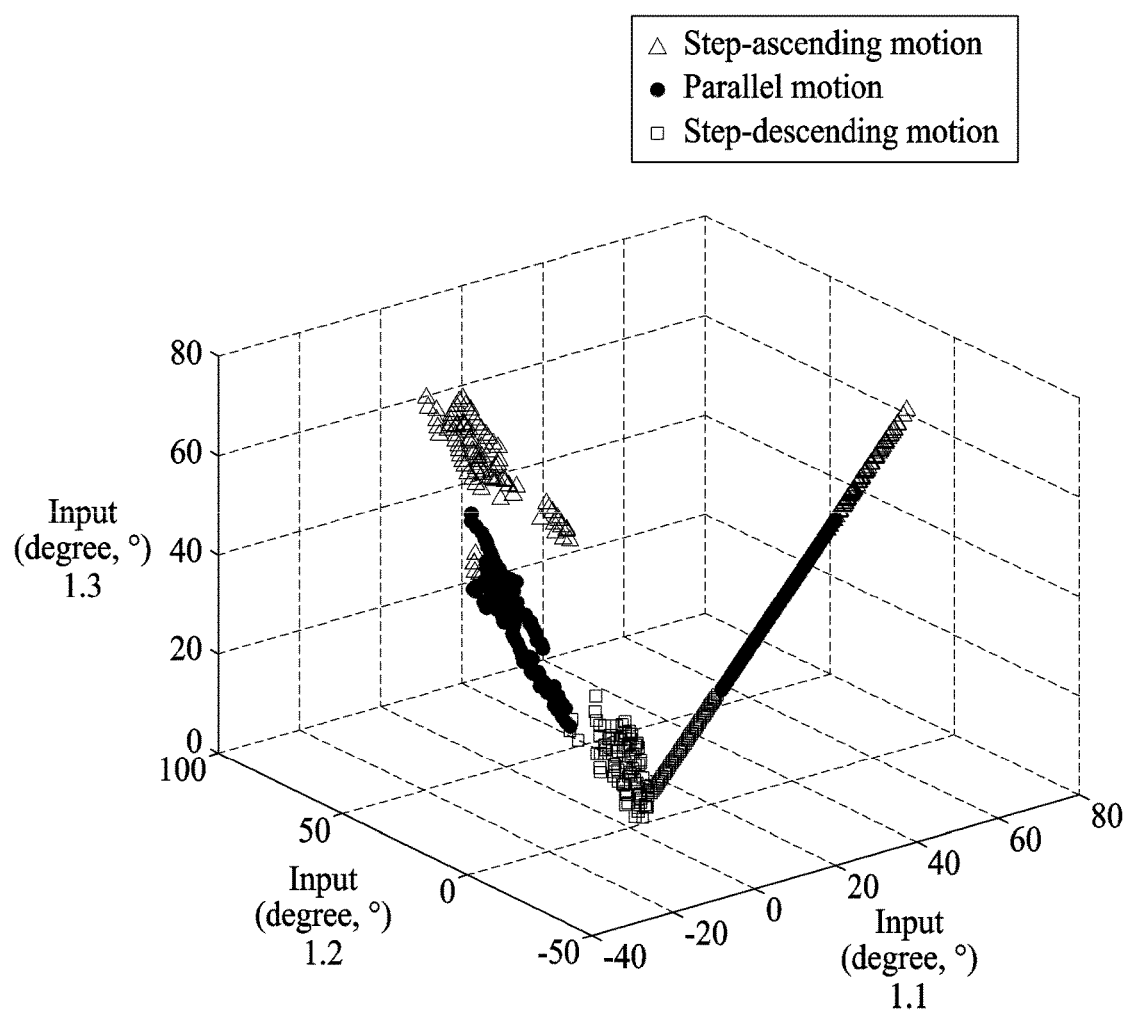
FIG. 6A illustrates an example of a graph to determine a gait task according to at least one example embodiment.

FIG. 6A illustrates an example of a graph to determine a gait task according to at least one example embodiment.

Referring to FIG. 6A, an input 1.1 may indicate a left hip joint angle, an input 1.2 may indicate a right hip joint angle, and an input 1.3 may indicate a difference between the left and right hip joint angles. FIG. 6A shows a distribution which represents the input 1.1, the input 1.2, and the input 1.3 on axes of the left hip joint angle, the right hip joint angle, and the difference between the left and right hip joint angles, respectively, with respect to a step-ascending motion, a parallel motion, and a step-descending motion.

Inputs may be classified into three groups. Each group may be formed based on a motion similarity. For example, a group of inputs indicated with triangles may correspond to the step-ascending motion, a group of inputs indicated with circles may correspond to the parallel motion, and a group of inputs indicated with rectangles may correspond to the step-descending motion.

A recognizer may be trained by machine learning using the left hip joint angle, the right hip joint angle, and/or the difference between the left and right hip joint angles as features. The step-ascending motion, the parallel motion, and the step-descending motion gait task may be classified based on distribution data of FIG. 6A.

Figure 6B:
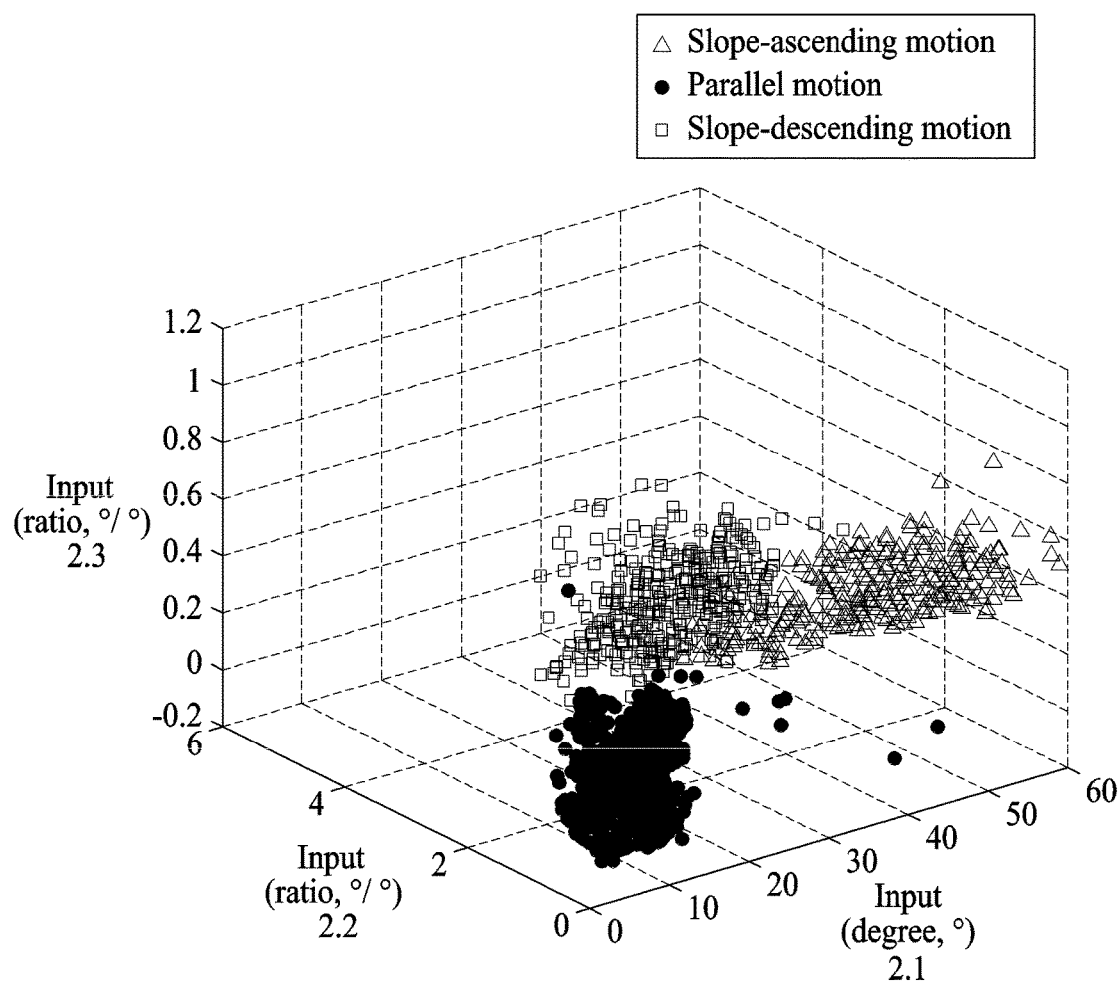
FIG. 6B illustrates another example of a graph to determine a gait task according to at least one example embodiment.

FIG. 6B illustrates another example of a graph to determine a gait task according to at least one example embodiment.

Referring to FIG. 6B, an input 2.1 may indicate a knee angle at a point in time at which angles of left and right knee joints become equal, an input 2.2 may indicate a ratio between a hip joint angle and a knee joint angle, and an input 2.3 may indicate a ratio between a knee angle at a point in time at which the left and right knee angles become equal and a maximum value of the knee angle. FIG. 6B shows a distribution, which represents the input 2.1, the input 2.2, and the input 2.3 on respective axes with respect to the slope-ascending motion, the parallel motion, and the slope-descending motion.

Inputs may be classified into three groups based on a motion similarity. For example, a group of inputs indicated with triangles may correspond to the slope-ascending motion, a group of inputs indicated with circles may correspond to the parallel motion, and a group of inputs indicated with rectangles may correspond to the slope-descending motion. The slope-ascending motion, the parallel motion, and the slope-descending motion may be classified from the input 2.1, the input 2.2, and the input 2.3 using a recognizer trained, for example, in advance, based on learning data of the slope-ascending motion, the parallel motion, and the slope-descending motion.

Figure 7:
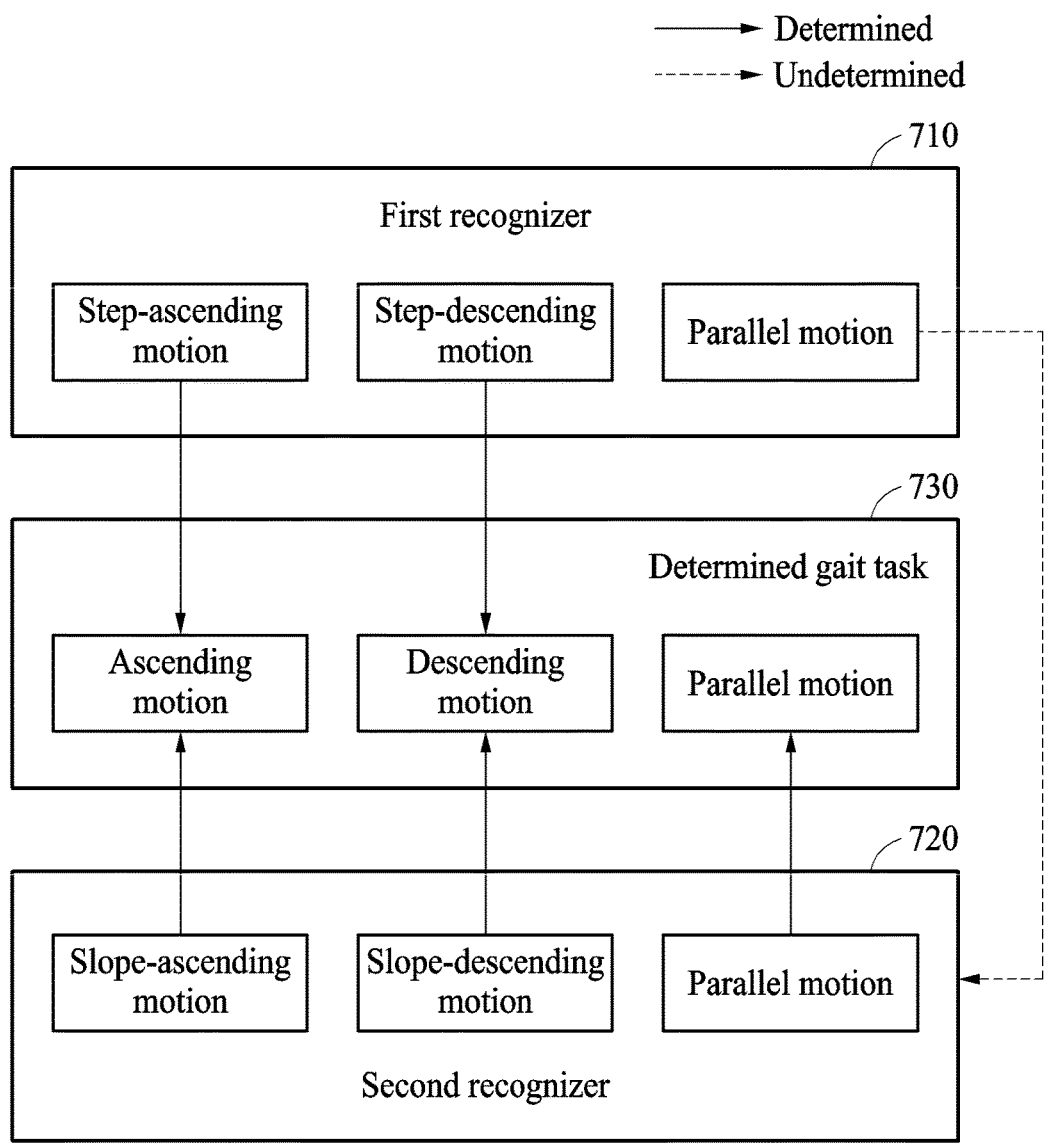
FIG. 7 illustrates another example of a method of controlling a walking assistance apparatus according to at least one example embodiment.

FIG. 7 illustrates another example of a method of controlling a walking assistance apparatus according to at least one example embodiment.

FIG. 7 illustrates an example embodiment of performing a second recognition phase only with respect to a parallel motion. In this example embodiment, the walking assistance apparatus may determine a gait task of a user as one of an ascending motion, a descending motion, or a parallel motion corresponding to a determined gait task 730 by sequentially performing a first recognition phase and a second recognition phase. The walking assistance apparatus may perform category classification into the ascending motion, the descending motion, or the parallel motion, and may determine a detailed scheme with respect to the parallel motion.

When a foot of the user is determined to be in contact with the ground, the walking assistance apparatus may determine a first gait task as a step-ascending motion, a step-descending motion, or the parallel motion using a first recognizer 710. The walking assistance apparatus may determine a motion, which is similar to the gait task of the user, from among the step-ascending motion, the step-descending motion, and the parallel motion based on first joint motion information using the first recognizer 710. For example, the first joint motion information may include a left hip joint angle, a right hip joint angle, and/or a difference between the left and right hip joint angles.

When the first gait task is determined as the parallel motion, the walking assistance apparatus may determine a second gait task as a slope-ascending motion, a slope-descending motion, or a parallel motion based on second joint motion information using a second recognizer 720. For example, the second joint motion information may include a ratio between a hip joint angle and a knee angle on the side on which the foot is in contact with the ground, a difference between the left and right knee angles, a minimum value or a maximum value of left and right hip joint angles, and/or a ratio between a knee angle at a point in time at which the left and right knee angles become equal and a maximum value of the knee angle.

When the first gait task is determined as the step-ascending motion or the step-descending motion, the step-ascending motion may be immediately confirmed as the ascending motion and the step-descending motion may be immediately confirmed as the descending motion.

Figure 8:
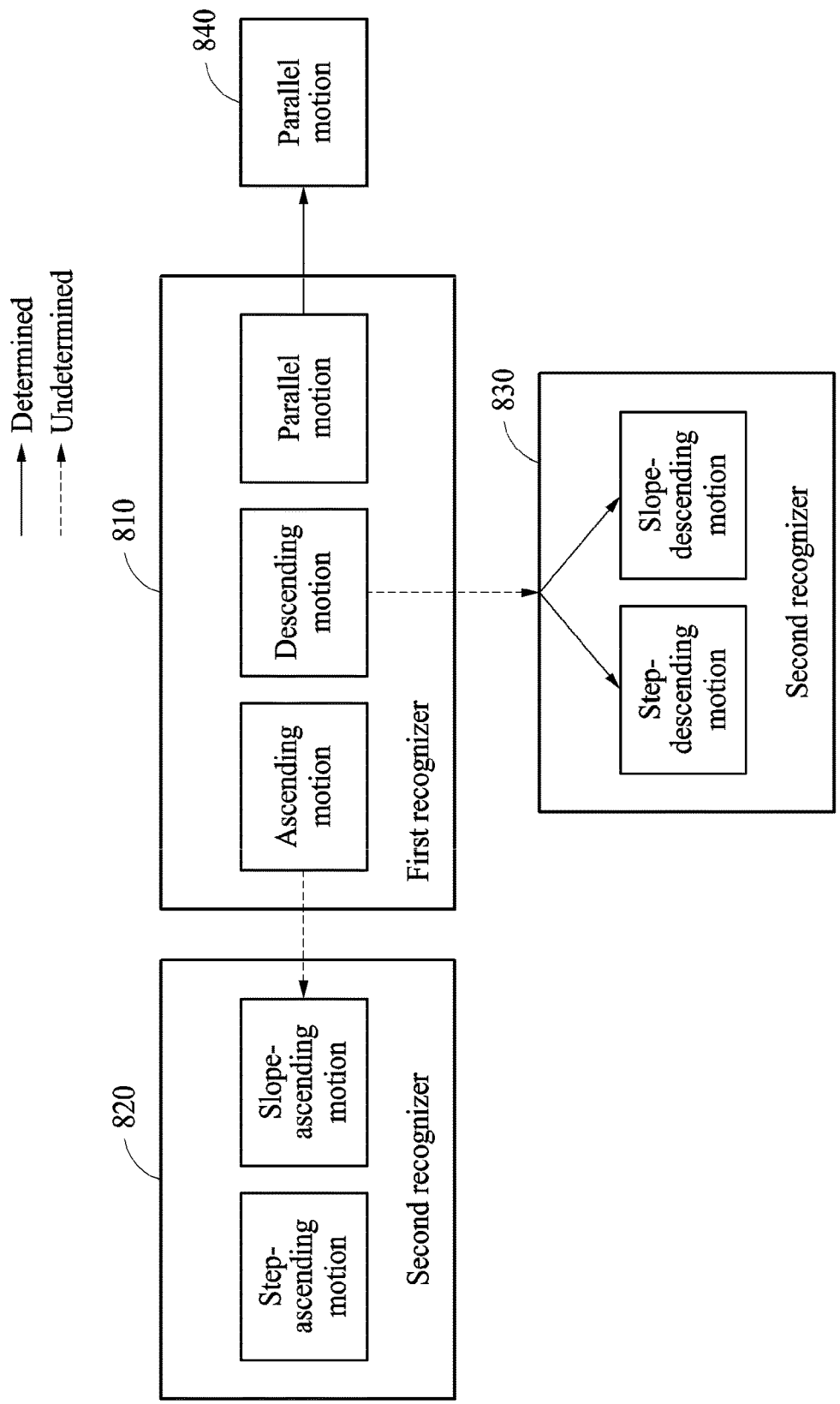
FIG. 8 illustrates another example of a method of controlling a walking assistance apparatus according to at least one example embodiment.

FIG. 8 illustrates another example of a method of controlling a walking assistance apparatus according to at least one example embodiment.

FIG. 8 illustrates an example embodiment of performing a second recognition phase with respect to each of an ascending motion and a descending motion. In this example embodiment, the walking assistance apparatus may determine a gait task of a user as one of a step-ascending motion, a step-descending motion, a slope-ascending motion, a slope-descending motion, or the parallel motion by sequentially performing a first recognition phase and the second recognition phase. The walking assistance apparatus may perform category classification into the ascending motion, the descending motion, or the parallel motion, and may determine a detailed scheme with respect to the ascending motion or the descending motion.

When a foot of the user is determined to be in contact with the ground, the walking assistance apparatus may determine a first gait task as the ascending motion, the descending motion, or the parallel motion using a first recognizer 810. The walking assistance apparatus may determine a motion, which is similar to the gait task of the user, among the ascending motion, the descending motion, and the parallel motion based on first joint motion information using the first recognizer 810. For example, the first joint motion information may include a left hip joint angle, a right hip joint angle, and/or a difference between the left and right hip joint angles.

When the first gait task is determined as the ascending motion, the walking assistance apparatus may determine a second gait task as a step-ascending motion or a slope-ascending motion using a first-second recognizer 820. For example, first-second joint motion information may include a difference between a hip joint angle and a knee angle on a side on which the foot is in contact with the ground, a larger value between left and right knee angles, and/or a difference between left and right ankle angles.

When the first gait task is determined as the descending motion, the walking assistance apparatus may determine the second gait task as a step-descending motion or a slope-descending motion using a second-second recognizer 830. For example, second-second joint motion information may include an average speed of an ankle on the side on which the foot is in contact with the ground during a desired (or alternatively, predetermined) period of time before the contact point in time.

When the first gait task is determined as the parallel motion, the gait task of the user may be immediately confirmed as a parallel motion 840.

Figure 9:
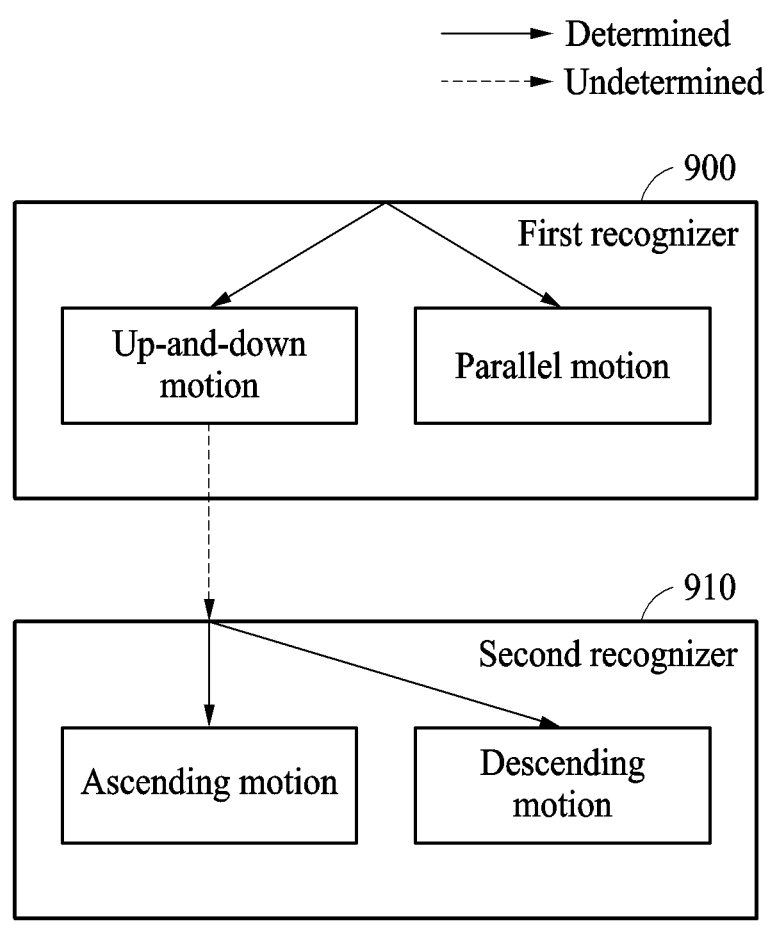
FIG. 9 illustrates another example of a method of controlling a walking assistance apparatus according to at least one example embodiment.

FIG. 9 illustrates another example of a method of controlling a walking assistance apparatus according to at least one example embodiment.

FIG. 9 illustrates an example embodiment of performing a second recognition phase with respect to each of an up-and-down motion and a parallel motion. In this example embodiment, the walking assistance apparatus may determine a gait task of a user as one of an ascending motion, a descending motion, or a parallel motion by sequentially performing a first recognition phase and the second recognition phase. The walking assistance apparatus may perform category classification into the up-and-down motion or the parallel motion, and may determine a detailed scheme with respect to each category.

When a foot of the user is determined to be in contact with the ground, the walking assistance apparatus may determine a first gait task as the up-and-down motion or the parallel motion using a first recognizer 900. The walking assistance apparatus may determine a motion, which is similar to the gait task of the user between the up-and-down motion and the parallel motion, using the first recognizer 900 based on first joint motion information.

When the first gait task is determined as the up-and-down motion, the walking assistance apparatus may determine a second gait task as the ascending motion or the descending motion using a second recognizer 910.

Figure 10:
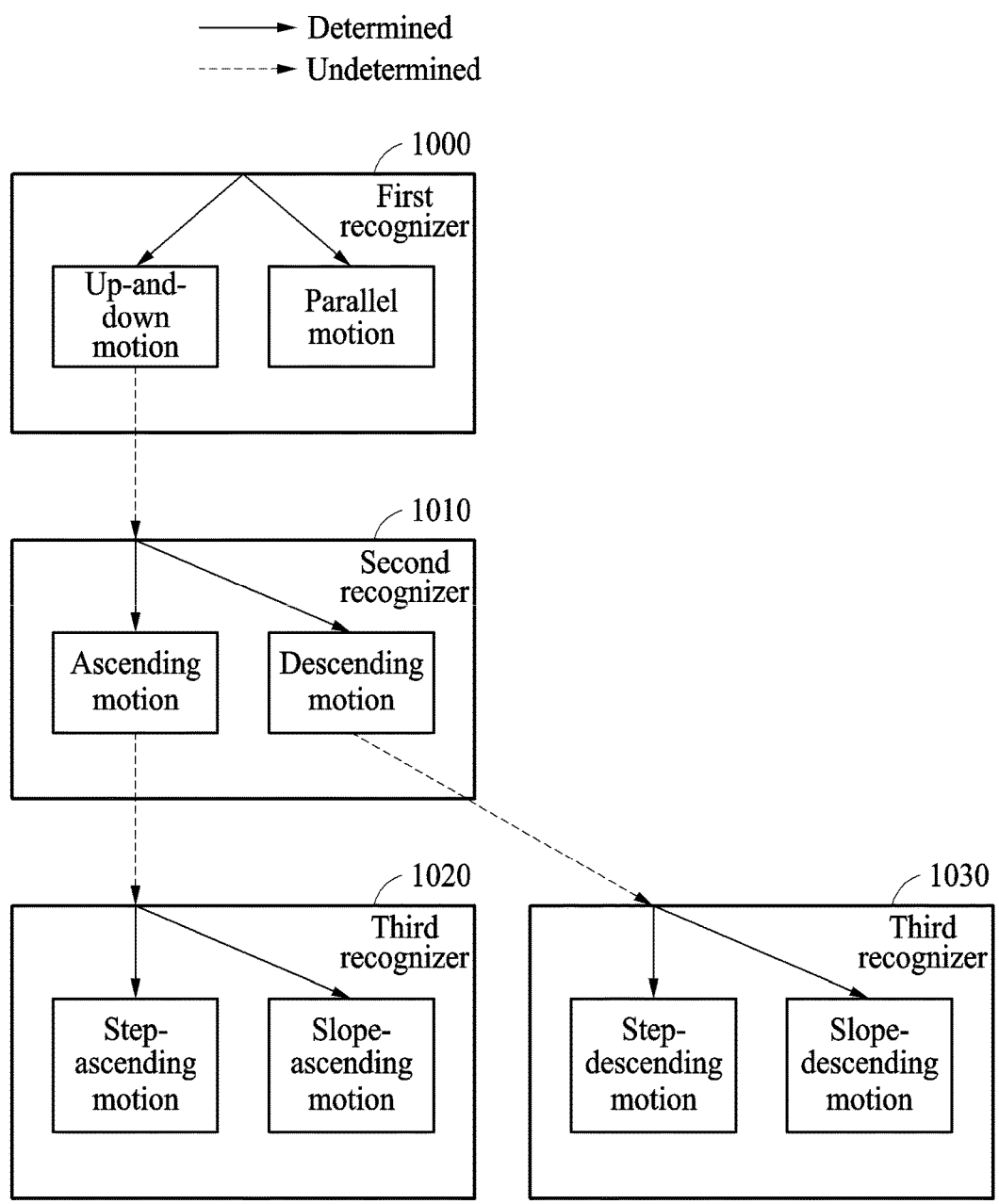
FIG. 10 illustrates another example of a method of controlling a walking assistance apparatus according to at least one example embodiment.

FIG. 10 illustrates another example of a method of controlling a walking assistance apparatus according to at least one example embodiment.

FIG. 10 illustrates another example embodiment of performing a second recognition phase with respect to an up-and-down motion, and then performing a third recognition phase with respect to each of an ascending motion and a descending motion. In this example embodiment, the walking assistance apparatus may determine a gait task of a user as one of a slope-ascending motion, a step-ascending motion, a slope-descending motion, a step-descending motion, or the parallel motion by sequentially performing a first recognition phase, the second recognition phase, and the third recognition phase. The walking assistance apparatus may perform category classification into the up-and-down motion or the parallel motion, may perform category classification into the ascending motion or the descending motion with respect to the up-and-down motion, and may determine a detailed scheme with respect to the ascending motion or the descending motion.

When a foot of the user is determined to be in contact with the ground, the walking assistance apparatus may determine a first gait task as the up-and-down motion or the parallel motion using a first recognizer 1000. The walking assistance apparatus may determine a motion, which is similar to the gait task of the user, between the up-and-down motion and the parallel motion using the first recognizer 1000 based on first joint motion information.

When the first gait task is determined as the up-and-down motion, the walking assistance apparatus may determine a second gait task as the ascending motion or the descending motion using a second recognizer 1010. The walking assistance apparatus may determine a motion, which is similar to the gait task of the user, between the ascending motion and the descending motion using the second recognizer 1010 based on second joint motion information.

The walking assistance apparatus may determine a third gait task of the user using third recognizers 1020 and 1030 (e.g., a first-third recognizer 1020 and a second-third recognizer 1030) based on third joint motion information associated with the determined second gait task and a contact point in time. When the second gait task is determined as the ascending motion, the walking assistance apparatus may determine the third gait task as the step-ascending motion or the slope-ascending motion. When the second gait task is determined as the descending motion, the walking assistance apparatus may determine the third gait task as the step-descending motion or the slope-descending motion.

The units and/or modules described herein may be implemented using hardware components and software components. For example, the hardware components may include microphones, amplifiers, band-pass filters, audio to digital converters, and processing devices. A processing device may be implemented using one or more hardware device configured to carry out and/or execute program code by performing arithmetical, logical, and input/output operations. The processing device(s) may include a processor, a controller and an arithmetic logic unit, a digital signal processor, a microcomputer, a field programmable array, a programmable logic unit, a microprocessor or any other device capable of responding to and executing instructions in a defined manner. The processing device may run an operating system (OS) and one or more software applications that run on the OS. The processing device also may access, store, manipulate, process, and create data in response to execution of the software. For purpose of simplicity, the description of a processing device is used as singular; however, one skilled in the art will appreciated that a processing device may include multiple processing elements and multiple types of processing elements. For example, a processing device may include multiple processors or a processor and a controller. In addition, different processing configurations are possible, such a parallel processors.

The software may include a computer program, a piece of code, an instruction, or some combination thereof, to independently or collectively instruct and/or configure the processing device to operate as desired, thereby transforming the processing device into a special purpose processor. Software and data may be embodied permanently or temporarily in any type of machine, component, physical or virtual equipment, computer storage medium or device, or in a propagated signal wave capable of providing instructions or data to or being interpreted by the processing device. The software also may be distributed over network coupled computer systems so that the software is stored and executed in a distributed fashion. The software and data may be stored by one or more non-transitory computer readable recording mediums.

The methods according to the above-described example embodiments may be recorded in non-transitory computer-readable media including program instructions to implement various operations of the above-described example embodiments. The media may also include, alone or in combination with the program instructions, data files, data structures, and the like. The program instructions recorded on the media may be those specially designed and constructed for the purposes of example embodiments, or they may be of the kind well-known and available to those having skill in the computer software arts. Examples of non-transitory computer-readable media include magnetic media such as hard disks, floppy disks, and magnetic tape; optical media such as CD-ROM discs, DVDs, and/or Blue-ray discs; magneto-optical media such as optical discs; and hardware devices that are specially configured to store and perform program instructions, such as read-only memory (ROM), random access memory (RAM), flash memory (e.g., USB flash drives, memory cards, memory sticks, etc.), and the like. Examples of program instructions include both machine code, such as produced by a compiler, and files containing higher level code that may be executed by the computer using an interpreter. The above-described devices may be configured to act as one or more software modules in order to perform the operations of the above-described example embodiments, or vice versa.

Some example embodiments of the inventive concepts having thus been described, it will be obvious that the same may be varied in many ways. Such variations are not to be regarded as a departure from the intended spirit and scope of example embodiments of the inventive concepts, and all such modifications as would be obvious to one skilled in the art are intended to be included within the scope of the following claims.

What is claimed is:

1. A method of controlling a walking assistance apparatus, the method comprising:
   determining, by a processor included in the walking assistance apparatus, whether a foot of a user wearing the walking assistance apparatus, which is configured to measure a joint motion of the user, is in contact with ground based on first joint motion information including a vertical acceleration of a pelvis;
   determining, by the processor, a first gait task of the user based on second joint motion information, the second joint motion information associated with a contact point in time at which the foot is in contact with the ground;
   determining, by the processor, a second gait task of the user based on third joint motion information, the third joint motion information associated with the first gait task and the contact point in time; and
   controlling, by the processor, the walking assistance apparatus based on at least one of the first gait task or the second gait task.

2. The method of claim 1, wherein the second joint motion information includes at least one of a left hip joint angle associated with the contact point in time, a right hip joint angle associated with the contact point in time, or a difference between the left hip joint angle and the right hip joint angle.

3. The method of claim 1, wherein the determining whether the foot of the user is in contact with ground comprises:
   determining whether the foot of the user is in contact with the ground based on the first joint motion information, the first joint motion information being information measured in a remaining time period, the remaining time period being a value excluding a certain time period after a previous contact point in time from a time period between the previous contact point in time and a current contact point in time.

4. The method of claim 3, wherein the determining whether the foot of the user is in contact with ground comprises:
   determining a point in time at which an average acceleration value of the vertical acceleration of the pelvis in the remaining time period is greater than or equal to a threshold as the current contact point in time.

5. The method of claim 1, wherein
   the determining a first gait task comprises determining the first gait task as an ascending motion, a descending motion, or a parallel motion, and
   the determining a second gait task comprises,
   determining the second gait task as a step-ascending motion or a slope-ascending motion in response to the first gait task determined as the ascending motion,
   determining the second gait task as a step-descending motion or a slope-descending motion in response to the first gait task determined as the descending motion, and
   determining the second gait task as the slope-ascending motion, the slope-descending motion, or the parallel motion in response to the first gait task determined as the parallel motion.

6. The method of claim 5, wherein
   the third joint motion information includes at least one of a first difference between a hip joint angle and a knee angle on a side on which the foot is in contact with the ground, a larger value between left and right knee angles, or a second difference between left and right ankle angles in response to the first gait task determined as the ascending motion,
   the third joint motion information includes an average speed of an ankle on the side on which the foot is in contact with the ground during a period of time before the contact point in time in response to the first gait task determined as the descending motion, and
   the third joint motion information includes at least one of a first ratio between the hip joint angle and the knee angle on the side on which the foot is in contact with the ground, a third difference between the left and right knee angles, a first minimum value or a first maximum value of left and right hip joint angles, or a second ratio between the knee angle at a point in time at which the left and right knee angles become equal and a second maximum value of the knee angle in response to the first gait task determined as the parallel motion.

7. The method of claim 1, wherein
   the determining a first gait task comprises determining the first gait task as an ascending motion, a descending motion, or a parallel motion, and
   the determining a second gait task comprises determining the second gait task as a slope-ascending motion, a slope-descending motion, or the parallel motion in response to the first gait task determined as the parallel motion.

8. The method of claim 7, wherein, when the third joint motion information includes at least one of a first ratio between a hip joint angle and a knee angle on a side on which the foot is in contact with the ground, a difference between left and right knee angles, a first minimum value or a first maximum value of left and right hip joint angles, or a second ratio between the knee angle at a point in time at which the left and right knee angles become equal and a second maximum value of the knee angle.

9. The method of claim 1, wherein
   the determining a first gait task comprises determining the first gait task as an ascending motion, a descending motion, or a parallel motion, and
   the determining a second gait task comprises,
   determining the second gait task as a step-ascending motion or a slope-ascending motion in response to the first gait task determined as the ascending motion, and
   determining the second gait task as a step-descending motion or a slope-descending motion in response to the first gait task determined as the descending motion.

10. The method of claim 1, wherein
    the determining a first gait task comprises determining the first gait task as an up-and-down motion or a parallel motion, and
    the determining a second gait task comprises determining the second gait task as an ascending motion or a descending motion in response to the first gait task determined as the up-and-down motion.

11. The method of claim 1, further comprising:
determining a third gait task of the user based on fourth joint motion information, the fourth joint motion information associated with the second gait task and the contact point in time,
wherein the controlling comprises controlling the walking assistance apparatus based on the first gait task, second gait task, and third gait task,
the determining a first gait task comprises determining the first gait task as an up-and-down motion or a parallel motion,
the determining a second gait task comprises determining the second gait task as an ascending motion or a descending motion in response to the first gait task determined as the up-and-down motion, and
the determining a third gait task comprises,
   determining the third gait task as a step-ascending motion or a slope-ascending motion in response to the second gait task determined as the ascending motion, and
   determining the third gait task as a step-descending motion or a slope-descending motion in response to the second gait task determined as the descending motion.

12. The method of claim 1, wherein the determining whether the foot of the user is in contact with the ground comprises determining whether the foot is in contact with the ground based on foot sensor information measured from a foot sensor included in the walking assistance apparatus.

13. A non-transitory computer-readable recording medium storing a program, which when executed by a computer, configures the computer to perform a method of comprising:
determining whether a foot of a user wearing the walking assistance apparatus, which is configured to measure a joint motion of the user, is in contact with ground based on first joint motion information including a vertical acceleration of a pelvis;
determining a first gait task of the user based on second joint motion information, the second joint motion information associated with a contact point in time at which the foot is in contact with the ground;
determining a second gait task of the user based on third joint motion information, the third joint motion information associated with the first gait task and the contact point in time; and
controlling the walking assistance apparatus based on at least one of the first gait task or the second gait task.

14. A walking assistance apparatus comprising:
a memory configured to store computer-readable instructions; and
at least one processor configured to execute the computer-readable instructions such that the at least one processor is configured to,
determine whether a foot of a user wearing the walking assistance apparatus, which is configured to measure a joint motion of the user, is in contact with ground based on first joint motion information including a vertical acceleration of a pelvis,
determine a first gait task of the user based on second joint motion information, the second joint motion information associated with a contact point in time at which the foot is in contact with the ground,
determine a second gait task of the user based on third joint motion information, the third joint motion information associated with the first gait task and the contact point in time, and
control the walking assistance apparatus based on at least one of the first gait task or the second gait task.

* * * * *